(12) United States Patent
Tamir

(10) Patent No.: US 10,596,573 B2
(45) Date of Patent: Mar. 24, 2020

(54) DEVICES FOR BIOLOGICAL SAMPLE COLLECTION AND ANALYSIS AND METHODS OF USE THEREOF

(71) Applicant: Bio-Marketing-T, Ltd. (BMT), Or-Akiva (IL)

(72) Inventor: Idan Tamir, Zichron Ya'akov (IL)

(73) Assignee: Bio-Marketing-T, Ltd. (BMT), Or-Akiva (IL)

( * ) Notice: Subject to any disclaimer, the term of this patent is extended or adjusted under 35 U.S.C. 154(b) by 135 days.

(21) Appl. No.: 15/548,971

(22) PCT Filed: Feb. 17, 2016

(86) PCT No.: PCT/IB2016/000296
§ 371 (c)(1),
(2) Date: Aug. 4, 2017

(87) PCT Pub. No.: WO2016/132223
PCT Pub. Date: Aug. 25, 2016

(65) Prior Publication Data
US 2018/0021771 A1  Jan. 25, 2018

Related U.S. Application Data

(60) Provisional application No. 62/117,211, filed on Feb. 17, 2015.

(51) Int. Cl.
*B01L 3/00* (2006.01)
*G01N 33/558* (2006.01)
(Continued)

(52) U.S. Cl.
CPC .......... *B01L 3/5029* (2013.01); *B01L 3/5023* (2013.01); *C12M 1/30* (2013.01); *C12Q 1/14* (2013.01);
(Continued)

(58) Field of Classification Search
CPC ....... B01L 2300/161; B01L 2400/0406; B01L 3/5023; B01L 3/5029; B01L 2300/0825;
(Continued)

(56) References Cited

U.S. PATENT DOCUMENTS 5,494,801 A * 2/1996 Bogart ................. A61K 39/092
422/534
5,916,802 A    6/1999 Berthold
(Continued)

FOREIGN PATENT DOCUMENTS

WO     9504280 A1   2/1995
WO     9800712 A1   1/1998
(Continued)

OTHER PUBLICATIONS

International Search Report for PCT Application No. PCT/IB2016/000296, dated Jul. 14, 2016.
(Continued)

*Primary Examiner* — Christine H Matthews
*Assistant Examiner* — Joshua Daryl D Lannu
(74) *Attorney, Agent, or Firm* — Greenberg Traurig, LLP

(57) ABSTRACT

In some embodiments, the present invention is a device, including: a swab including an absorptive component attached to a stem, an extraction chamber configured to receive the swab and position the absorptive component of the swab configured to be in fluid communication with an extraction reagent, a test strip configured to be brought in fluid communication with the extraction reagent following extraction of the analyte from the biological sample, including: a sample receiving portion configured to accept a sample, a site on the strip where the analyte-specific labeled reagent has been incorporated, such reagent configured to bind the analyte from the biological sample, a capture portion configured to receive: the analyte from the biological
(Continued)

sample and the analyte-specific labeled reagent so as to result in displaying a positive or negative result at the completion of the assay, and an adsorbent pad attached to the test strip.

18 Claims, 5 Drawing Sheets

(51) Int. Cl.
| | |
|---|---|
| *G01N 33/543* | (2006.01) |
| *C12M 1/30* | (2006.01) |
| *C12Q 1/14* | (2006.01) |
| *G01N 33/538* | (2006.01) |
| *G01N 33/569* | (2006.01) |
| *G01N 33/53* | (2006.01) |

(52) U.S. Cl.
CPC ....... *G01N 33/5302* (2013.01); *G01N 33/538* (2013.01); *G01N 33/543* (2013.01); *G01N 33/558* (2013.01); *G01N 33/56944* (2013.01); *B01L 2300/0825* (2013.01); *B01L 2300/16* (2013.01); *B01L 2300/161* (2013.01); *B01L 2400/0406* (2013.01)

(58) Field of Classification Search
CPC .... B01L 2300/16; C12M 1/30; G01N 33/538; G01N 33/543; G01N 33/558; G01N 33/5302; G01N 33/56944; C12Q 1/14
See application file for complete search history.

(56) References Cited

U.S. PATENT DOCUMENTS

| | | |
|---|---|---|
| 2003/0207442 A1 | 11/2003 | Markovsky et al. |
| 2007/0292902 A1 | 12/2007 | Cheng et al. |
| 2008/0199851 A1 | 8/2008 | Egan et al. |
| 2008/0299648 A1* | 12/2008 | Tomer .................. C12Q 1/04 435/287.7 |

FOREIGN PATENT DOCUMENTS

| | | |
|---|---|---|
| WO | 0054024 A1 | 9/2000 |
| WO | 2013019817 A1 | 2/2013 |
| WO | 2013108250 A1 | 7/2013 |

OTHER PUBLICATIONS

Extended European Search Report to corresponding EP Application No. 16751983.4 dated Aug. 13, 2018 (9 pages).

* cited by examiner

DEVICES FOR BIOLOGICAL SAMPLE COLLECTION AND ANALYSIS AND METHODS OF USE THEREOF

RELATED APPLICATIONS

This application is a 371 National Phase Application of International Application No. PCT/IB2016/000296, filed Feb. 17, 2016, which claims the priority of U.S. Provisional Patent Application Ser. No. 62/117,211, filed Feb. 17, 2015, the contents of which are all incorporated by reference in their entireties.

TECHNICAL FIELD

In some embodiments, the present instant invention is related to detection tests, which are diagnostic tests which can be used in assisting in the diagnosis of bacterial pharyngitis caused by group A streptococci (GAS) and methods of use thereof.

BACKGROUND

Group A *Streptococcus* (*Streptococcus Pyogenes*) typically causes acute upper respiratory tract infection. Early diagnosis and treatment of Group A Streptococcal pharyngitis is critical for reducing the severity of symptoms and complications, such as rheumatic fever and glomerulonephritis, and preventing the rare but possible occurrence of death—of the 9,000-11,500 cases of invasive disease (3.2 to 3.9/100,000 population) that occur each year in the United States alone, 10%-15% result in death. Typical diagnostic tests used for assaying Group A *Streptococcus* antigens require the mixing of equal to or more than two reagents and/or use laborious test-specific protocols.

SUMMARY OF INVENTION

In some embodiments, the present invention is a device, including:
  a swab including an absorptive component attached to a stem, where the absorptive component includes a non-volatile reagent,
  an extraction chamber configured to receive the swab and position the absorptive component of the swab configured to be in fluid communication with an extraction reagent,
  where the extraction chamber is filled with an extraction reagent,
  a test strip configured to be brought in fluid communication with the extraction reagent following extraction of the analyte from the biological sample, including:
  a sample receiving portion configured to accept a sample, usually a liquid sample, and permit the movement of any analyte in the liquid through the test strip via, e.g., but not limited to, capillary action,
  a site on the strip where the analyte-specific labeled reagent has been incorporated, such reagent configured to bind the analyte from the biological sample, and includes any molecule that binds the analyte specifically and with high affinity and is further labeled with a label that allows its detection,
  a capture portion configured to receive: the analyte from the biological sample and the analyte-specific labeled reagent so as to result in displaying a positive or negative result at the completion of the assay, and
  an adsorbent pad attached to the distal end of the test strip and configured to bind to an excess extraction reagent thereby allowing flow across the test strip.

In some embodiments, the analyte is *Streptococcus* Group A Carbohydrate Antigen. In some embodiments, the extraction reagent is a nitrite salt. In some embodiments, the extraction reagent is 0.2-5 M nitrite salt solution. In some embodiments, the non-volatile reagent is acidic.

In some embodiments, the swab and test strip are configured to be in fluid communication, so as to result in capillary flow from the absorptive component of the swab to a sample receiving portion of the test strip. In some embodiments, the stem may be solid, porous, or any combination thereof. In some embodiments, the stem is configured to provide: mechanical support for the absorptive component of the swab, and capillary flow through a porous core of the stem. In some embodiments, the absorptive component of the swab is composed of a fiber, foam of polymeric material, absorbent material, or any combination thereof. In some embodiments, the acidic non-volatile reagent is deposited at the absorptive component of the swab by: spraying, dipping, or dispersing the absorptive component of the swab in a solvent containing the acidic non-volatile reagent, and evaporating the solvent.

In some embodiments, the amount of the acidic non-volatile reagent is between 2 and 800 micromoles. In some embodiments, the acidic non-volatile reagent is soluble in the extraction reagent. In some embodiments, the acidic non-volatile reagent is insoluble in the extraction reagent. In some embodiments, the acidic non-volatile reagent is configured to exchange protons with the extraction reagent. In some embodiments, the insoluble acidic non-volatile reagent is deposited on the swab in a region configured to attach to the absorptive component, and where the insoluble acidic non-volatile reagent is deposited on the swab by coating with a membrane or film made of a polymeric material prior to the application of the absorptive component, so as to result in avoiding direct contact between the acid and the subject. In some embodiments, the acidic non-volatile reagent is organic. In some embodiments, the acidic non-volatile reagent is inorganic. In some embodiments, the device includes: a first structural component configured to attach the absorptive component of the swab by the stem of the swab, a second structural component configured to house the test strip, where the absorptive component and a sample receiving portion of the test strip are in liquid communication when joining the first structural component and the second structural component.

In some embodiments, the present invention is a method, including:
  (i) collecting a biological sample of a subject by use of a swab including a first, non-volatile reagent;
  (ii) transferring the swab to a chamber containing an extraction reagent, so as to allow the non-volatile reagent to react with the extraction reagent and result in generating an extraction solution;
  (iii) extracting an analyte from the biological sample of the subject by the extraction solution;
  (iv) contacting the extraction solution containing the extracted analyte with a lateral flow immunochromatographic assay device including a labeled analyte-specific indicator; and
  (v) determining a presence or absence of the extracted analyte in the biological sample of the subject,
  where the binding of the analyte- to a capture reagent immobilizes the labeled analyte-indicator complex on the lateral flow immunochromatographic assay device, and where the capture reagent is configured to specifically bind to the analyte.

In some embodiments, the present invention is a method, including:
(i) collecting a biological sample of a subject by an absorptive component of a swab, where the absorptive component of the swab is configured to be in physical contact with a sample receiving portion of a lateral flow immunochromatographic assay test strip including a labeled analyte-specific indicator;
(ii) transferring the absorptive component of the swab to a chamber containing an extraction reagent, where an extraction solution is formed in-situ by the reaction of the extraction reagent with the second non-volatile reagent incorporated in the absorptive component of the swab, and where the extraction solution is configured to extract the biological sample of the subject;
(iii) extracting an analyte from the biological sample;
(iv) determining the presence or absence of the extracted analyte in the biological sample of the subject by measuring a signal generated by a binding of a labeled analyte-indicator complex to a capture reagent, where the capture reagent is immobilized on the lateral flow immunochromatographic assay device, and where the capture reagent is configured to specifically bind to the analyte.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIG. 1 shows an embodiment of the device of the present invention, which is a side view of a typical swab, comprised of stem and tip (i.e., the absorptive component), indicating reagent incorporation sites.

FIG. 4 shows detail of a preferred embodiment of the integrated swab-test strip device of the present invention, providing physical contact between the swab and test strip, thereby allowing capillary liquid communication between the two.

Figures 1A, 1B:
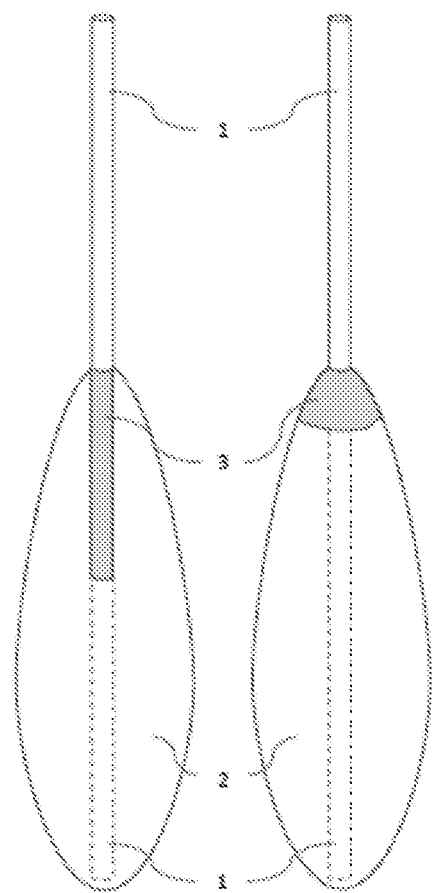
FIG. 1A depicts reagent application by coating the swab's stem.
FIG. 1B depicts reagent incorporation into the swab tip's area that is away from the sample collection zone.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DESCRIPTION OF EXEMPLARY EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, a "lateral flow test" refer to an immunochromatographic device intended to detect the presence (or absence) of a target analyte in sample (matrix) without the need for specialized and costly equipment. Typically, these tests are used for medical diagnostics either for home testing, point of care testing, or laboratory use.

As used herein, a "sample receiving portion" or a "fluid receiving portion" refers to a portion of a test strip configured to accept a sample, usually a liquid/fluid sample, and permit the movement of any analyte in the liquid/fluid through the test strip via, e.g., but not limited to, capillary action.

As used herein, an "analyte-specific labeled reagent" or a "labeled analyte-specific indicator" are synonymous and refer to what is commonly known in the diagnostic literature as a "conjugate"—a dried form of bio-active particles in a salt-sugar matrix that contains everything to guarantee an optimized chemical reaction between the target molecule (e.g., the analyte) and its chemical partner (e.g., antibody) that has been immobilized on the particle's surface As used herein, a "capture portion" or "capture zone" refers to a portion of a test strip where analyte-reagent complexes bind to a capture reagent (e.g., but not limited to, an analyte-specific antibody).

As used herein, "sorptivity" refers to a measure of the capacity of the medium to absorb or desorb liquid by capillarity.

In some embodiments, the device of the present invention is configured to measure the presence or absence of *Streptococcus* Group A antigen in a biological sample. In some embodiments, the device comprises: (i) a swab (e.g., a throat swab) for use in collecting a biological sample, (ii) an extraction chamber containing an extraction reagent, and (iii) a test strip. In some embodiments, the swab is comprised of a stem and tip (absorptive component), where the tip incorporates a non-volatile reagent configured to extract, or aid in extracting, at least one analyte.

In some embodiments, the extraction solution formed by the dissolution of the non-volatile reagent incorporated in the swab's tip in the extraction reagent serves to extract the analyte.

In some embodiments, the method of the present invention is comprised of: (i) collecting a biological sample by a swab; (ii) transferring it to a chamber containing an extraction reagent, where this extraction reagent is complemented by an additional/second reagent incorporated in the swab (e.g., but not limited to the tip of the swab), where the extraction reagent, when combined with the additional reagent incorporated in the swab, is configured to dissolve and/or react in-situ with the collected biological sample and extract the antigen/analyte from the biological sample; (iii) contacting the extraction solution containing the extracted analyte with a lateral flow immunochromatographic assay device containing a labeled analyte-specific indicator; and (iv) determining the presence or absence of the extracted analyte in the biological sample by measuring a signal (i.e., the presence or absence of the signal) generated by a binding of a labeled analyte-indicator complex to a capture reagent, where the capture reagent is immobilized on the lateral flow immunochromatographic assay device, and where the capture reagent is configured to specifically bind to the analyte.

In some embodiments, the present invention is a device for collecting and analyzing a biological or clinical sample, the device being comprised of (i) a swab, (ii) an extraction chamber containing an extraction reagent, and (iii) a test strip. In some embodiments, the swab is comprised of: (i) a stem made of a plastic or other material, which may be solid or porous, which is configured to provide mechanical support for the swab tip and optionally also promote liquid transfer via capillary flow through the stem's porous core; (ii) a tip at one end of the stem made of fiber or foam of polymeric material or other absorbent material coated or spun or otherwise deposited on the stem's end (taken together, stem and tip are termed: "swab"). In case the stem is made from porous material, the whole swab may be manufactured from the same foam or other porous material thereby simplifying its manufacturing process, and (iii) a non-volatile reagent that comprises an essential component of the solution used to extract, or aid in extracting, the sample being collected by the swab and is (a) coated onto the swab stem in the area underlying its tip or (b) incorporated within the swab's tip absorbent material. In some embodiments, the extraction chamber comprises an elongated tube having, for example, but not limited to: (i) a rounded, v-shaped, or flat bottom geometry and (2) a 4-10 mm inner diameter, where the extraction chamber is configured to allow substantially simultaneous accommodation of both swab tip and test strip. In some embodiments, the test strip is a conventional, lateral flow, immunochromatographic assay device. In some embodiments, the non-volatile material is a water-soluble organic acid. In some embodiments, the non-volatile material is a water-soluble inorganic acid. In some embodiments, the non-volatile material is an insoluble acidic polymer.

In some embodiments, the amount of the non-volatile acidic material is in the range of 50 and 800 micromoles. In some embodiments, the amount of the non-volatile acidic material is in the range of 100 and 800 micromoles. In some embodiments, the amount of the non-volatile acidic material is in the range of 150 and 800 micromoles. In some embodiments, the amount of the non-volatile acidic material is in the range of 200 and 800 micromoles. In some embodiments, the amount of the non-volatile acidic material is in the range of 250 and 800 micromoles. In some embodiments, the amount of the non-volatile acidic material is in the range of 300 and 800 micromoles. In some embodiments, the amount of the non-volatile acidic material is in the range of 350 and 800 micromoles. In some embodiments, the amount of the non-volatile acidic material is in the range of 400 and 800 micromoles. In some embodiments, the amount of the non-volatile acidic material is in the range of 450 and 800 micromoles. In some embodiments, the amount of the non-volatile acidic material is in the range of 500 and 800 micromoles. In some embodiments, the amount of the non-volatile acidic material is in the range of 550 and 800 micromoles. In some embodiments, the amount of the non-volatile acidic material is in the range of 600 and 800 micromoles. In some embodiments, the amount of the non-volatile acidic material is in the range of 650 and 800 micromoles. In some embodiments, the amount of the non-volatile acidic material is in the range of 700 and 800 micromoles. In some embodiments, the amount of the non-volatile acidic material is in the range of 750 and 800 micromoles.

In some embodiments, the amount of the non-volatile acidic material is in the range of 2 and 750 micromoles. In some embodiments, the amount of the non-volatile acidic material is in the range of 2 and 700 micromoles. In some embodiments, the amount of the non-volatile acidic material is in the range of 2 and 650 micromoles. In some embodiments, the amount of the non-volatile acidic material is in the range of 2 and 600 micromoles. In some embodiments, the amount of the non-volatile acidic material is in the range of 2 and 550 micromoles. In some embodiments, the amount of the non-volatile acidic material is in the range of 2 and 500 micromoles. In some embodiments, the amount of the non-volatile acidic material is in the range of 2 and 450 micromoles. In some embodiments, the amount of the non-volatile acidic material is in the range of 2 and 400 micromoles. In some embodiments, the amount of the non-volatile acidic material is in the range of 2 and 350 micromoles. In some embodiments, the amount of the non-volatile acidic material is in the range of 2 and 300 micromoles. In some embodiments, the amount of the non-volatile acidic material is in the range of 2 and 250 micromoles. In some embodiments, the amount of the non-volatile acidic material is in the range of 2 and 200 micromoles. In some embodiments, the amount of the non-volatile acidic material is in the range of 2 and 150 micromoles. In some embodiments, the amount of the non-volatile acidic material is in the range of 2 and 100 micromoles. In some embodiments, the amount of the non-volatile acidic material is in the range of 2 and 50 micromoles. In some embodiments, the amount of the non-volatile acidic material is in the range of 2 and 10 micromoles. In some embodiments, the amount of the non-volatile acidic material is in the range of 5 and 10 micromoles. In some embodiments, the amount of the non-volatile acidic material is in the range of 3 and 5 micromoles.

In some embodiments, the amount of the non-volatile acidic material is in the range of 30 and 200 micromoles. In some embodiments, the amount of the non-volatile acidic material is in the range of 50 and 200 micromoles. In some embodiments, the amount of the non-volatile acidic material is in the range of 100 and 200 micromoles. In some embodiments, the amount of the non-volatile acidic material is in the range of 150 and 200 micromoles. In some embodiments, the amount of the non-volatile acidic material is in the range of 30 and 150 micromoles. In some embodiments, the amount of the non-volatile acidic material is in the range of 30 and 100 micromoles. In some embodiments, the amount of the non-volatile acidic material is in the range of 30 and 50 micromoles.

In some embodiments, the swab and test strip are integrated into a single device by contacting the back end of the swab tip (i.e., the absorptive component) to the sample pad of the test strip allowing for capillary liquid communication between both media.

In some embodiments, the present invention is a method for determining the presence or absence of an analyte in a sample, comprising the following steps: (a) collecting a biological sample using a swab incorporating an non-volatile compound that comprises a component of the sample extraction solution, (b) extracting the analyte from the sample in an assay chamber containing an extraction reagent, (c) interacting the extraction solution containing the extracted analyte with a lateral flow immunochromatographic assay test strip, by: (i) inserting this test strip into the extraction solution or (ii) transferring the extraction solution contents to the device by means of a valve, pipette or any other common means of fluid transfer; (d) allowing the formation of analyte-labeled reagent complexes by the reaction of the analyte flowing through the lateral flow device with the analyte-specific labeled reagent carried by the device; (e) determining the presence or absence of the analyte in the sample by the presence or absence of a signal formed by the binding of the analyte-labeled reagent complex to an analyte-specific capture reagent immobilized at the lateral flow device detection zone. In some embodiments, the analyte is Strep A antigen. In some embodiments, the extraction reagent is 0.2 M to 5M nitrite salt solution.

In some embodiments, the extraction reagent is 1 M to 5 M nitrite salt solution. In some embodiments, the extraction reagent is 2 M to 5 M nitrite salt solution. In some embodiments, the extraction reagent is 3 M to 5 M nitrite salt solution. In some embodiments, the extraction reagent is 4 M to 5 M nitrite salt solution. In some embodiments, the extraction reagent is 0.2 M to 4 M nitrite salt solution. In some embodiments, the extraction reagent is 0.2 M to 3 M nitrite salt solution. In some embodiments, the extraction reagent is 0.2 M to 2 M nitrite salt solution. In some embodiments, the extraction reagent is 0.2 M to 1 M nitrite salt solution. In some embodiments, the extraction reagent is 1 M to 2 M nitrite salt solution. In some embodiments, the extraction reagent is 1.5 M to 2 M nitrite salt solution. In some embodiments, the extraction reagent is 1 M to 1.5 M nitrite salt solution. In some embodiments, the extraction reagent is 3 M to 4 M nitrite salt solution.

In some embodiments, the device of the present invention relates to immunoassays involving *Streptococcus* Group A carbohydrate antigen extraction prior to assay performance by individuals typically lacking extensive training in laboratory techniques. In some embodiments, the device is configured to render transfer of the extracted sample to the immunoassay device for analysis unnecessary. In some embodiments, the device of the present invention is configured to allow the use of a swab carrying at least one analyte extraction solution component. In some embodiments, the at least one analyte extraction solution component is a non-volatile dry solid (e.g. citric acid), and is incorporated into the swab. In some embodiments, the device is configured to simplify the steps of analyte extraction processing, by reducing the number of reagent solutions and assay steps. In some embodiments, the amount of (a) non-volatile reagent immobilized on the swab and (b) extraction reagent in the extraction chamber are pre-aliquoted onto the device. In some embodiments, the device of the present invention reduces errors due to incorrect reagent dispensing and sample transfer steps. In some embodiments, device of the present invention is configured to detect the presence or absence of *Streptococcus* Group A antigen in swab samples, e.g., throat swab samples.

Typically, the device and methods of the present invention allow for the detection of analytes in samples which need to be extracted or otherwise chemically manipulated prior to assay performance, while simplifying the sample extraction process and reducing sample manipulation.

The device of the present invention is configured for collecting a biological or a clinical sample, the device being comprised of a stem made of plastic or similar supportive material and a tip, located at one end of the stem, made of fiber or foam or other absorbent material coated or spun or otherwise deposited on the stem's end (taken together, stem and tip constitute the "swab"). In some embodiments, deposited non-volatile material is either coated onto the swab stem in the area directly underlying its tip or incorporated within the stem tip's absorbent material. In some embodiments, the non-volatile material is configured for use in extracting and/or treating the biological/clinical sample collected onto the swab.

In some embodiments, the present invention is a method for determining the presence or absence of *Streptococcus* Group A antigen in a sample, comprising the following steps: (a) collecting a biological sample using a throat swab incorporating a non-volatile acid; (b) extracting the antigen from the sample in an assay chamber containing a extraction reagent, where the extraction reagent is a nitrite salt aqueous solution, (c) interacting the extraction solution containing the extracted analyte (Strep A polysaccharide antigen) with a lateral flow immunochromatographic assay device, where the interaction is allowed by (i) insertion of a lateral flow test strip into the extraction solution or by (ii) transferring the extraction solution contents to the assay device by means of a valve, pipette, capillary forces, or any other known means of fluid transfer; (d) allowing the formation of analyte-labeled reagent complexes by the reaction of the analyte flowing through the lateral flow device with the labeled analyte-specific reagent carried by the lateral flow device; (e) determining the presence or absence of the analyte in the sample by the presence or absence of a signal formed by the binding of the analyte-labeled reagent complex to an analyte-specific capture reagent immobilized at the lateral flow device detection zone, or any combination thereof.

In some embodiments, the present invention is a device, where the device is configured to allow conducting an immunoassay for extracted *Streptococcus* Group A carbohydrate antigens. In some embodiments, the transfer of an extracted sample fluid to the immunoassay device for analysis is not required. In some embodiments, contact between the extraction solution and the diagnostic strip is sufficient for assay performance. In some embodiments, the lateral flow immunochromatographic assay methods of the present invention can be performed using commercially available test strips. In some embodiments, the device of the present invention is configured to use swabs carrying at least one analyte extraction solution component(s), wherein the analyte extraction reagent component can be in the form of a non-volatile dry solid applied to the swab by means of incorporation. In some embodiments, the device reduces analyte extraction process complexity and reduces the number of required reagents and assay steps. In some embodiments, the device is configured to allow analyte extraction and analysis within a single chamber using a single, pre-filled extraction reagent. In some embodiments, the device is configured to be used without the need for either swab or extraction solution removal from the extraction chamber for assay performance.

EXAMPLES

In order for the advantages of the invention to be readily understood, a more particular description of the disclosure briefly described above will be rendered by reference to specific embodiments that are illustrated in the appended drawing(s). It is noted that the drawings of the disclosure may not be to scale and are merely schematic representations, not intended to portray specific parameters of the disclosure. It is to be understood that these drawing(s) depict only typical embodiments of the disclosure and are not therefore to be considered to be limiting of its scope, the disclosure will be described and explained with additional specificity and detail through the use of the accompanying drawing(s), in which:

FIG. 1 shows an embodiment of the device of the present invention, including a swab, comprised of a stem (1) and a rounded tip made of absorbent material (2) for clinical sample collection, with the tip incorporating a non-volatile reagent essential for efficient analyte extraction from the sample. Reagent incorporation (3) can be performed by coating the swab's stem (FIG. 1A) or on the back end of the swab's tip at the tip-stem boundary, away from the sample collection zone (FIG. 1B). It should be noted that other reagent incorporation schemes are possible and the current illustrations merely serve as examples, depicting preferred incorporation sites.

Figure 2:
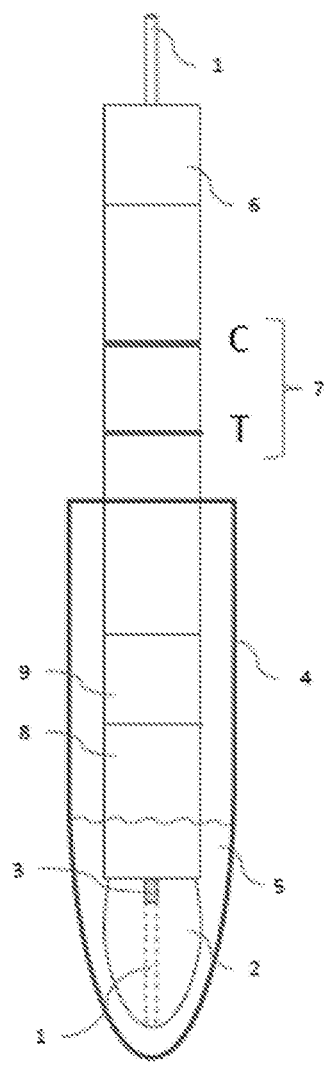
FIG. 2 shows an embodiment of the device of the present invention, which is a side view of a diagnostic kit that includes a swab, extraction chamber and test strip, indicating the relative positions of each of the components.

FIG. 2 shows an embodiment of the device of the present invention, in which extraction of Strep A antigen is carried out by inserting the modified throat swab (1-2) carrying a clinical sample into an extraction chamber (4) containing a pre-aliquoted solution of nitrite salt (extraction reagent) (5). The acid incorporated within the swab tip (3) dissolves in and acidifies the nitrite salt solution, thereby creating a solution of nitrous acid (extraction solution). This process promotes extraction of the polysaccharide-based Strep A antigen, which is further enhanced by thoroughly mixing the swab tip (2) in the extraction solution (5). The swab may then be kept in the extraction chamber (4) while the extraction solution containing the extracted analyte is brought in contact with the lateral flow strip (6-9). This can be accomplished by dipping the sample pad of the test strip (8) in the extraction solution without removing the swab from the extraction chamber. The buffer optionally incorporated into the sample pad of the test strip acts to neutralize the analyte-carrying acidic extraction solution. The extracted analyte travels by capillary forces from the test strip's sample pad to the site on the strip where the analyte-specific labeled reagent has been incorporated (9), thereby solubilizing this reagent and forming labeled analyte-reagent complexes. These complexes continue to flow through the test strip, driven by capillary forces until they reach the capture zone (7) where they bind to an immobilized capture reagent (usually another analyte-specific reagent/antibody, specific for either the analyte (T) or the mobile labeled reagent itself (C)). This binding event results in the accumulation of the label at the capture zone, which is visually detectable or can be monitored by the use of a dedicated reader, providing an indication for the presence of the analyte in the sample (T) and to the test's proper performance (C). Excess extraction solution is wicked by the adsorbent pad (6) located at the distal end of the lateral flow test strip, which drives capillary flow along the test strip membrane. In some embodiments, the swab tip can serve three distinct functions: (i) collecting a biological or clinical sample, e.g., bacterial colonies from a patient's throat; (ii) incorporating swab tip-adsorbed non-volatile reagent; and (iii) co-transferring both the biological/clinical sample and swab-incorporated non-volatile reagent to the extraction reagent to effect efficient analyte extraction.

In an embodiment, the extraction chamber's dimensions, geometry and optical properties are selected to allow assay performance within the extraction chamber without transferring either the extraction fluid or the extracted swab from the extraction chamber. Since swab tip diameters and test strip widths commonly range around 4 mm (e.g., but not limited to, 3 mm-6 mm), an extraction chamber is configured to have an inner diameter of 4-10 mm for the performance of both analyte extraction and immunochromatographic assay. Typically, commercial swab tip's length range is 10-30 mm and the volume of the extraction fluid should therefore be adjusted accordingly to allow sufficient swab tip coverage by the extraction reagent to optimize analyte extraction. In an exemplary embodiment, using a 5 mm inner diameter cylindrical extraction chamber and a 15 mm tipped swab, the minimal extraction solution volume can be 250 uL allowing sufficient swab tip coverage for optimal analyte extraction. In some embodiments, the device of the present invention can use a typical extraction fluid volume present in commercially-available Strep A tests of 250-500 uL, which can be compatible with performing the extraction and assay steps within a single chamber.

In some embodiments, extraction chamber's geometry can be cylindrical, rectangular or any other shape that properly accommodates both the swab and the test strip. In some embodiments, the device is comprised of materials including glass and inert plastics (e.g., but not limited to, polypropylene, polyethylene, polyethylene terephthalate, polystyrene, polycarbonate, etc., or any combination thereof) that exhibit minimal binding of the extracted analyte to be analyzed. In some embodiments, optically-transparent materials are used for extraction chamber walls for test results visualization. In some embodiments, extraction chamber length can be adjusted to allow the results reading area on the test strip to protrude out of the extraction chamber aperture to allow results visualization (FIG. 2). In some embodiments, the extraction chamber bottom can be rounded, v-shaped, flat or any other shape that is configured to accommodate both the swab tip and test strip, either alone or when present together. In some embodiments, the use of rounded or v-shaped geometries reduces the volume required for optimal swab tip coverage. In some embodiments, the use of rounded or v-shaped geometries improves co-accommodation of the test strip and the swab tip (see FIG. 2). In some embodiments, the extraction chamber is capped allowing its pre-filling by an accurate amount of the extraction reagent, which assists in transport of the diagnostic kit to the site where the test is to be conducted, and uncapping the extraction chamber immediately prior to introduction of the swab carrying the biological sample.

In another embodiment of the device of the present invention, the fluid contents of the extraction chamber can be transferred for analysis to a test strip contained within a lateral flow device by means of a valve or any other common mean of gravitational or capillary fluid transfer.

Figure 3:
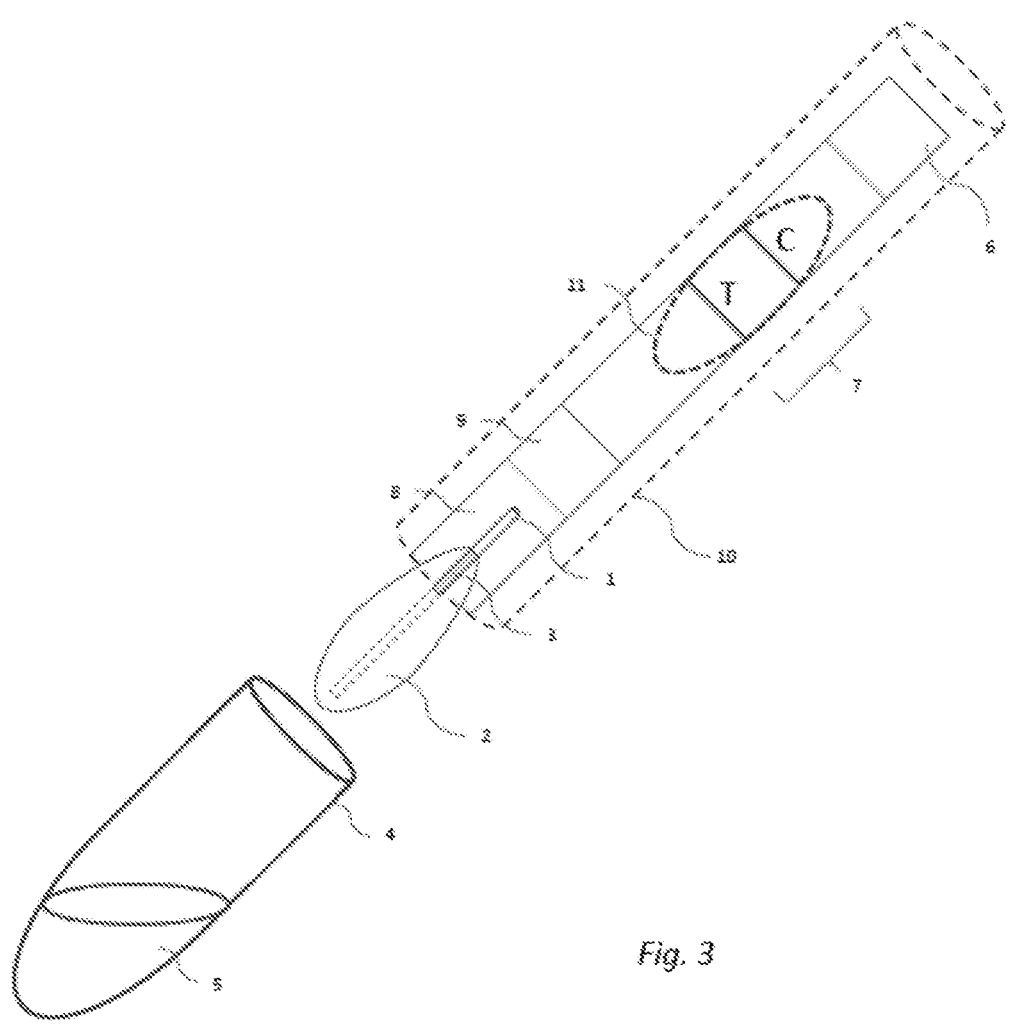
FIG. 3 shows an embodiment of the device of the present invention, which is a perspective view of a cross section of a diagnostic kit that includes an extraction chamber and an integrated swab-test strip device that connects the back end of the swab tip to the sample pad of the test strip allowing for capillary liquid communication between both media; the integrated device is enclosed within a cylindrical shaped casing that also acts as a handle for the integrated device, replacing the swab's stem for grip and allowing sample collection and analysis within the same integrated device.

FIG. 3 shows an embodiment of the present invention, where the swab carrying the incorporated non-volatile reagent (1-3) and the test strip (6-9) are integrated into a single device by connecting the back end of the swab tip (2) to the sample pad of the test strip (8) allowing for capillary liquid communication between both media. This integrated device unifies the swab and diagnostic strip allowing clinical sample collection and analysis in a single device. This configuration reduces the diagnostic procedure's complexity by removing the requirement for test strip addition to the extraction chamber following analyte extraction (as depicted in FIG. 2). In this exemplary embodiment, introduction of the swab tip (2) into the extraction reagent (5) present in the extraction chamber (4) results in wicking of the extraction reagent into the swab tip. This leads to solubilization of the non-volatile reagent carried by the swab tip (3) into the extraction reagent solution, which in turn provides the optimal conditions for efficient in-situ extraction of the analyte present on the swab tip, and possibly reduces the need for swab tip stirring in the extraction reagent solution to effect efficient analyte extraction. Extracted analyte then travels by capillary forces from the swab's tip into the test strip's sample pad (8), where it is optionally neutralized by a buffer incorporated into this area of the test strip. The extracted analyte continues to travel by capillary forces from the test strip's sample pad to the site on the strip where the analyte-specific labeled reagent has been incorporated (9), thereby solubilizing this reagent which reacts with the analyte forming labeled analyte-reagent complexes. These complexes continue to flow through the test strip by capillary forces until they reach the capture zone (7) where the complexes can bind to an immobilized capture reagent (typically another analyte-specific reagent/antibody, specific for either the analyte (T) or the labeled reagent itself (C)). In this embodiment, the united swab-test strip is sheathed in a casing (10) that acts both as a handle, replacing the swab's stem for efficient clinical sample collection, and a cassette for the test strip. A window in this casing (11), which may be simply an opening or composed of, e.g., but not limited to, transparent plastic film, allows easy reading of test results. The casing (10) and the extraction chamber (4) are configured to match the casing outer diameter to the inner diameter of the extraction chamber, thereby allowing the casing to fit into and optionally cap the extraction chamber. Such capping can be affected by plugging the extraction chamber by the casing or by means of a screw joint or any other typical means of forming such junction. Such capping has the added advantage of sealing the extraction chamber and preventing spillage of the extraction reagent out of the extraction chamber. This also simplifies test disposal in one unit following results reading. In an embodiment, the swab tip can serve four functions: (i) collecting a biological or clinical sample, e.g., bacterial colonies from a patient's throat; (ii) incorporating swab tip-adsorbed non-volatile reagent that aids in analyte extraction; (iii) co-transferring of both biological/clinical sample and swab-incorporated non-volatile reagent to the extraction reagent to form the extraction solution and effect efficient analyte extraction; and (iv) providing fluid conduit allowing efficient capillary wicking of the extracted analyte solution to the test strip's sample pad for analysis.

Figure 4A:
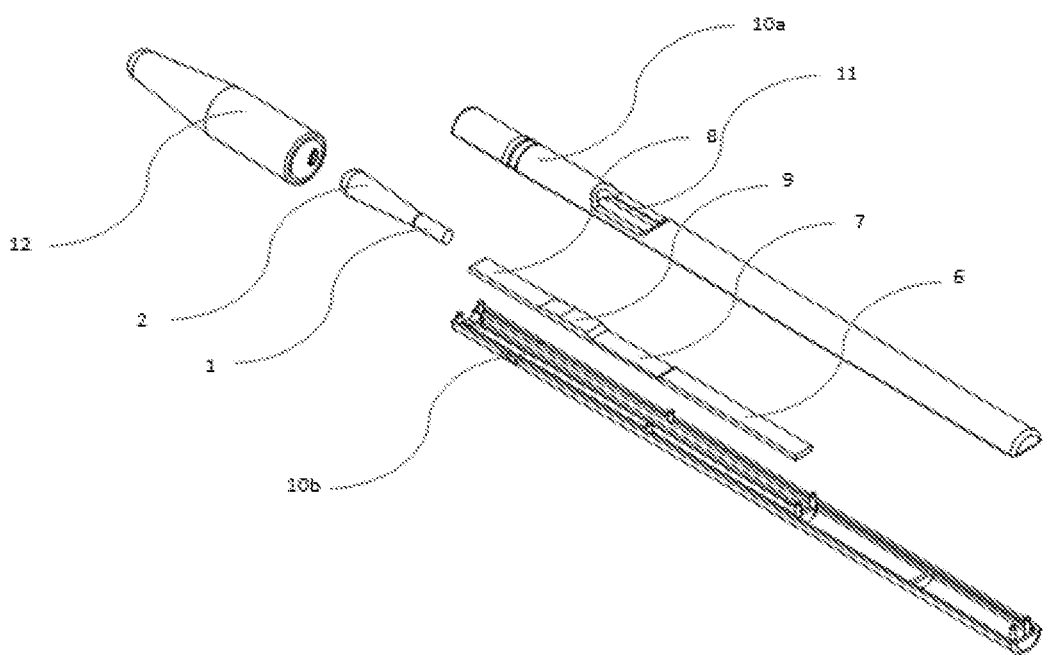
FIG. 4A shows a perspective view of the integrated device, displaying all major components.
Figure 4B:
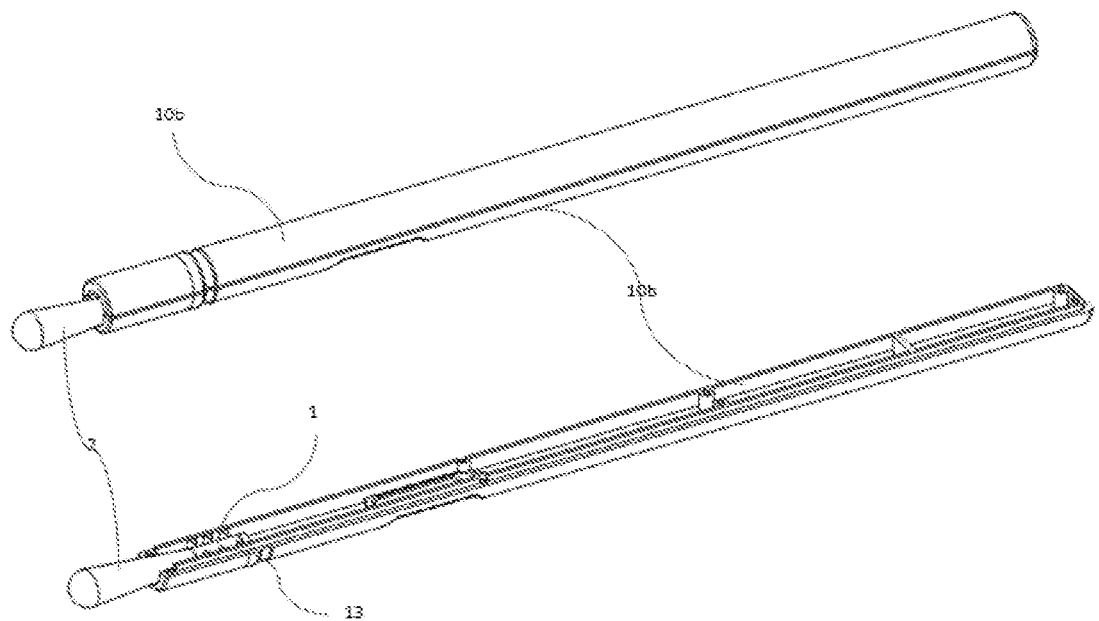
FIG. 4B provides additional detail for swab tip mechanical immobilization within the integrated device.
Figure 4C:
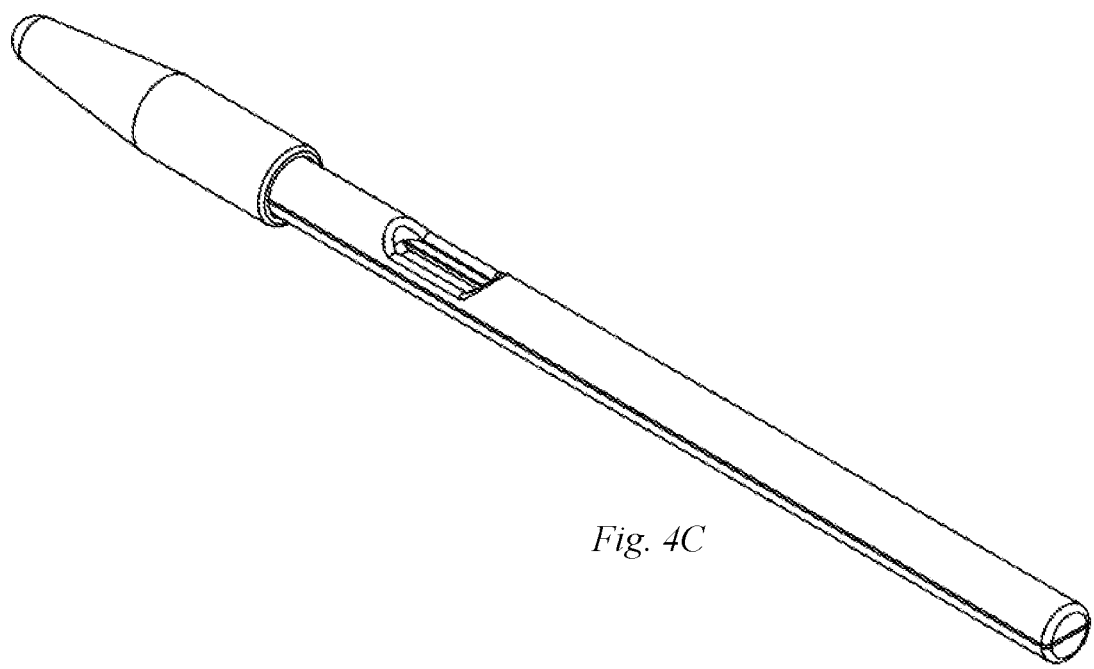
FIG. 4C shows the fully assembled integrated device.

FIG. 4A shows one integrated device configuration that enables swab tip—diagnostic strip integration involving a casing made up of two matching, interlocking valves (10a, b). One such valve—the cover (10a)—is configured to clasp the swab tip (2) via its stem (1), while the other valve—the base (10b)—is configured to accommodate the test strip (6-9). These two interlocking valves are designed to bring the swab tip (2) and the test strip's sample pad (8) in physical contact upon joining these two valves. The results window (11) in the casing allows direct visualization of diagnostic test results. The casing cap (12) that protects the swab tip from mechanical damage is being removed to expose the swab's tip immediately prior to clinical sample collection. FIG. 4B depicts further detail of the interaction between the casing cover (10a) and the swab stem (1), showing one possible clasping mechanism involving protrusions in the cover (13) that serve to firmly immobilize the swab stem within the casing cover. FIG. 4C depicts such fully assembled integrated device.

In some embodiments of the device of the present invention, the extraction reagent is made exclusively of solvent, e.g., but not limited to, water. In other embodiments, the extraction reagent is an aqueous solution, having nitrite salt concentration in the range of 0.2-5 M. The extraction reagent may also contain any typically-used, non-ionic, detergent (e.g., but not limited to, NONIDET P-40, Tween-20 Triton X-100, CHAPS, or any combination thereof), a pH buffering compound (e.g., but not limited to phosphate, Tris, HEPES, or any combination thereof), a chelating agent (e.g., but not limited to EDTA, EGTA, or any combination thereof), a preservative (e.g., but not limited to, thimerosal, chlorhexidine digluconate, sodium benzoate, potassium sorbate, sodium azide, sulfate salts of gentamicin, chloramphenicol and streptomycin, protease inhibitors or phenolic compounds, or any combination thereof), and a marker that changes the solution's color (e.g., but not limited to, from pink to light yellow) upon solubilization of the additional reagent incorporated in the swab. In some embodiments, analyte extraction from the sample is carried out by contacting the throat swab with 400 uL of 1.2 M sodium nitrite solution present in the extraction chamber. In some embodiments, the swab tip is stirred in the extraction reagent by turning the swab against the side of the tube. In some embodiments, after mixing the sample with the reagents, extraction is allowed to proceed for between 10 seconds and 120 seconds, to allow for adequate polysaccharide antigen extraction. In some embodiments, the extraction is allowed to proceed for between 10 seconds and 60 seconds, to allow for adequate polysaccharide antigen extraction. In some embodiments, the extraction is allowed to proceed for between 10 seconds and 30 seconds. In some embodiments, the extraction is allowed to proceed for between 30 seconds and 60 seconds. In some embodiments, the extraction is allowed to proceed for between 30 seconds and 120 seconds. In an embodiment, the swab is left in the extraction chamber while the test strip is introduced to it (FIG. 2). In another embodiment (FIG. 3), the analyte is extracted in situ at the swab's tip by the incoming extraction reagent that becomes acidified by the non-volatile acid incorporated in the swab's tip. In some embodiments, the configuration has the advantage of allowing additional contact time between the extraction reagent and the sample carried by the swab tip which optimizes antigen extraction.

In some embodiments of the device of the present invention, neutralization of the nitrous acid solution following extraction of the antigens is affected by a buffer material incorporated within the sample receiving portion (8) of the lateral flow immunochromatographic assay device (test strip). In an embodiment, analyte extraction and testing is performed within the same chamber without swab or fluid removal, introduction of the test strip into the extraction chamber following analyte extraction causes the buffer contained within the test strip to dissolve into the extraction solution thereby neutralizing the nitrous acid solution and allowing optimal lateral flow immunochromatographic assay performance.

In some embodiments of the device of the present invention, the amount of acid incorporated within the swab is between 2-800 micromoles. As will be apparent to a person knowledgeable in the art, the amount of acid that needs to be incorporated in the swab tip to allow for effective Strep A antigen extraction depends on several factors, including (but not limited to): i) degree of acid acidity (pKa), ii) acid solubilization rate iii) volume and concentration of the extraction reagent that is to be acidified, iv) assay performance scheme and details (with or without swab removal, or by using an integrated device, etc.). Each combination of the above factors needs to be empirically tested to assure optimal Strep A antigen extraction. As guideline for such optimal extraction may serve the pH range of the buffer resulting from mixing the two individual reagent solutions contained in typical rapid Strep A diagnostic tests, which is typically a pH from 4.5 to 4.7. In some embodiments, acid can be selected from edible or typically safe (GRAS) non-volatile organic acids, such as, but not limited to: citric, ascorbic, etc. In some embodiments, the acid allows the swab to be used directly in contact with the throat tissue. In some embodiments, the swab can be configured to have a depositing or coating of non-volatile acid in a location that does not come in direct contact with the throat tissue, such as on the swab's stem in the area directly underlying its tip or incorporated within the stem tip's absorbent material away from the area that is configured to come into contact with the throat tissue (FIG. 1). In some embodiments, the non-volatile acid can be co-incorporated with other inert agents (e.g., dextrose) to improve acid dissolution into the extraction buffer. In some embodiments, the non-volatile acid can be co-incorporated with other inert agents to improve taste (e.g., sweeteners, artificial flavors), or add coloring (e.g., food colorant). In some embodiments, the non-volatile acid can be co-incorporated with a mucolytic agent, such as N-acetylcysteine, to reduce sample viscosity. In some embodiments, the deposited non-volatile acid can be polymeric (e.g., but not limited to, polystyrene sulfonic acid, Nafion, etc.) and insoluble in the extraction reagent. In some embodiments, an ionic exchange between the acidic polymer and the extraction reagent result in the acidification of the latter without dissolution of the acidic polymer.

In some embodiments, the present invention is a device including a swab used for biological sample collection, where the swab can comprise, e.g., but not limited to, a polyester fiber (or fiber of other polymeric material) coated swab, foam swab, comprising open-cell polyurethane (e.g., but not limited to, Becton Dickinson foam swabs) or a flocked swab (e.g., but not limited to, swabs made by Copan). In some embodiments, to increase assay sensitivity, swab tips are constructed to adsorb minimal amount of analyte and retain minimal fluid volume when coupled to a test strip's sample pad, thereby maximizing sample transfer to the test strip for analysis. In some embodiments, this is achieved by proper selection and optimization of the following parameters: swab tip's construction material (e.g., but not limited to, polyester fiber), tip fiber diameter (e.g., but not limited to, 5-20 micron), fiber surface properties (e.g., but not limited to, hydrophilic coating), tip porosity (e.g., but not limited to, a porosity of 70-90%), tip length and diameter (typically, but not limited to 15-20 mm and 4-6 mm, respectively), and tip sorptivity. In some embodiments, tip sorptivity can be chosen to allow rapid and quantitative capillary fluid transfer from the extraction solution to the swab tip and from the swab tip to the test strip's sample pad. Such capillary fluid transfer may or may not be counteracted by gravitational forces—i.e., the device incorporating the swab and test strip may operate in either the vertical or horizontal positions. The respective sorptivity and porosity of the swab tip, the test strip's sample pad, and the additional membranes that are used to construct the lateral flow-based test strip need to be selected and/or adjusted to allow efficient and continuous liquid flow from the swab tip to the sample pad of the test strip and from there to the rest of the test strip components to allow for optimal device operation. Such selection and/or adjustment of device component's porosity and sorptivity should take into account the intended use of the device in terms of its vertical vs. horizontal positioning, for example, but not limited to, increasing capillary forces acting within device components to counteract external gravitational forces in devices designed to operate in the upright position.

In some embodiments, the swab can be prepared with a non-volatile acid by dipping, spraying, or otherwise dispersing a solution of such acid in a volatile solvent, followed by solvent evaporation. In some embodiments, when employing acidic polymers, one end of the swab stem (where the tip is to be constructed) can be pre-wrapped or coated with a membrane or film made of the acidic polymeric material prior to the application of the fiber (e.g., but not limited to, wool, cotton, polyester, or any other fibrous or otherwise absorbent material, e.g., but not limited to, a sponge) or foam matrix that is to create the tip (FIG. 1). In some embodiments, such configuration avoids direct physical contact between the acidic polymer carried by the swab and the throat tissue from which the biological sample is to be withdrawn for diagnosis.

In some embodiments, the present invention is a one-step immunochromatographic assay device configured to use commercially-available lateral-flow based test strips. In some embodiments, the immunochromatographic assay device can contain a sample receiving region comprising a porous material, configured to allow lateral flow of a sample containing extracted analytes from the sample receiving region to the analyte detection region. In some embodiments, the sample receiving region and the analyte detection region can be present on a single porous member, or may comprise at least two separate porous members in lateral flow contact. In some embodiments, the sample receiving region can contain dry analyte-specific labeled reagents that are solubilized by the extraction reagent allowing analyte-labeled reagent complex formation. In some embodiments, the labeled analyte-reagent complexes are configured to flow through the device by capillary forces until they reach the capture zone where they bind to the immobilized capture reagent, typically another analyte-specific antibody (i.e., a binding event). In some embodiments, the binding event is detectable visually or by the use of a dedicated reader by the accumulation of the label at the capture zone, which is configure to provide an indication of the presence of the analyte in the sample.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is being claimed is:

1. A device, comprising:
   an extraction chamber filled with an extraction reagent, wherein the extraction reagent includes a nitrite salt;
   a swab comprising an absorptive component attached to a stem, the absorptive component being configured to obtain a biological sample at a sampling location,
      wherein the absorptive component comprises a non-volatile reagent, wherein the non-volatile reagent is configured to react with the extraction reagent to produce an extraction solution, the extraction solution being configured to extract an analyte from the biological sample,
      wherein the non-volatile reagent comprises a dry solid that is incorporated into the swab,
   wherein the non-volatile reagent is acidic,
      wherein the swab is configured to be received within the extraction chamber so as to position the absorptive component of the swab in fluid communication with the extraction reagent so as to produce the extraction solution, and
   a test strip configured to be brought in fluid communication with the extraction solution following extraction of the analyte from the biological sample, the test strip comprising:
      a sample receiving portion configured to accept a sample,
         wherein the sample is a liquid sample, and
         wherein the sample receiving portion is configured to permit
      the movement of the analyte in the liquid sample through the test strip by capillary action,
      a site on the strip where an analyte-specific labeled reagent has been incorporated, wherein the analyte-specific labeled reagent is configured to bind the analyte from the biological sample, and
         wherein the analyte-specific labeled reagent comprises a molecule that is configured to bind the analyte specifically and with high affinity, and
         wherein the analyte-specific labeled reagent is labeled with a label that allows its detection,
      a capture portion configured to receive the analyte from the biological sample and the analyte-specific labeled reagent so as to result in displaying a positive or negative result at a completion of an assay, and
      an adsorbent pad attached to a distal end of the test strip and configured to bind to an excess extraction reagent thereby allowing flow across the test strip.

2. The device of claim 1, wherein the analyte is Streptococcus Group A Carbohydrate Antigen.

3. The device of claim 1, wherein the extraction reagent is 0.2-5M nitrite salt solution.

4. The device of claim 1, wherein the swab and test strip are configured to be in fluid communication, so as to result in capillary flow from the absorptive component of the swab to the sample receiving portion of the test strip.

5. The device of claim 1, wherein the stem is solid, porous, or any combination thereof.

6. The device of claim 1, wherein the stem is configured to provide:
   mechanical support for the absorptive component of the swab, and
   capillary flow through a porous core of the stem.

7. The device of claim 1, wherein the absorptive component of the swab is composed of a fiber, foam of polymeric material, absorbent material, or any combination thereof.

8. The device of claim 1, wherein the acidic non-volatile reagent is deposited at the absorptive component of the swab by:
   spraying, dipping, or dispersing the solvent containing the acidic non-volatile reagent onto the absorptive component of the swab, and
   evaporating a solvent.

9. The device of claim 1, wherein the amount of the acidic non-volatile reagent is between 2 and 800 micromoles.

10. The device of claim 1, wherein the acidic non-volatile reagent is soluble in the extraction reagent.

11. The device of claim 1, wherein the acidic non-volatile reagent is insoluble in the extraction reagent.

12. The device of claim 11, wherein the acidic non-volatile reagent is configured to exchange protons with the extraction reagent.

13. The device of claim 11, wherein the insoluble acidic non-volatile reagent is deposited on the swab in a region configured to attach to the absorptive component, and
   wherein the insoluble acidic non-volatile reagent is deposited on the swab by coating with a membrane or film made of a polymeric material prior to an application of the absorptive component, so as to result in avoiding direct contact between an acid and a subject.

14. The device of claim 1, wherein the acidic non-volatile reagent is organic.

15. The device of claim 1, wherein the acidic non-volatile reagent is inorganic.

16. The device of claim 1, wherein the device comprises:
   a first structural component configured to attach the absorptive component of the swab by the stem of the swab, and
   a second structural component configured to house the test strip,
   wherein the absorptive component and the sample receiving portion of the test strip are in liquid communication when joining the first structural component and the second structural component.

17. A method, comprising:
   (i) collecting a biological sample at a sampling location of a subject by use of a swab comprising a first, non-volatile reagent, wherein the non-volatile reagent comprises a dry solid that is incorporated into the swab;
   (ii) transferring the swab to a chamber containing an extraction reagent configured to react with the non-volatile reagent, so as to allow the non-volatile reagent to react with the extraction reagent and result in generating an extraction solution;
   (iii) extracting an analyte from the biological sample of the subject by the extraction solution;
   (iv) contacting the extraction solution containing the extracted analyte with a lateral flow immunochromatographic assay device comprising a labeled analyte-specific reagent; and
   (v) determining a presence or absence of the extracted analyte in the biological sample of the subject, wherein a binding of the analyte to a capture reagent specifically immobilizes a labeled analyte-indicator complex on the lateral flow immunochromatographic assay device, and wherein the capture reagent is configured to specifically bind to the analyte.

18. A method comprising:
(i) collecting a biological sample at a sampling location of a subject by an absorptive component of a swab,
wherein the absorptive component of the swab is configured to be in physical contact with a sample receiving portion of a lateral flow immunochromatographic assay test strip comprising a labeled analyte-specific reagent, and wherein the absorptive component of the swab includes a non-volatile reagent incorporated therein, wherein the non-volatile reagent comprises a dry solid that is incorporated into the swab;
(ii) transferring the absorptive component of the swab to a chamber containing an extraction reagent configured to react with the non-volatile reagent,
wherein an extraction solution is formed in-situ by the a reaction of the extraction reagent with a second non-volatile reagent incorporated in the absorptive component of the swab, and wherein the extraction solution is configured to extract the biological sample of the subject;
(iii) extracting an analyte from the biological sample;
(iv) determining a presence or absence of the extracted analyte in the biological sample of the subject by measuring a signal generated by a binding of a labeled analyte-indicator complex to a capture reagent,
wherein the capture reagent is immobilized on the lateral flow immunochromatographic assay device, and
wherein the capture reagent is configured to specifically bind the analyte.

* * * * *